(12) United States Patent
Castonguay

(10) Patent No.: US 7,256,895 B2
(45) Date of Patent: Aug. 14, 2007

(54) SPHERICAL SCATTERING-LIGHT DEVICE FOR SIMULTANEOUS PHASE AND INTENSITY MEASUREMENTS

(76) Inventor: Raymond J. Castonguay, 2441 S. Kevin Dr., Tucson, AZ (US) 85748

( * ) Notice: Subject to any disclaimer, the term of this patent is extended or adjusted under 35 U.S.C. 154(b) by 234 days.

(21) Appl. No.: 10/788,094

(22) Filed: Feb. 26, 2004

(65) Prior Publication Data

US 2004/0165189 A1 Aug. 26, 2004

Related U.S. Application Data

(60) Provisional application No. 60/450,185, filed on Feb. 26, 2003, provisional application No. 60/452,300, filed on Mar. 5, 2003.

(51) Int. Cl.
*G01B 9/02* (2006.01)

(52) U.S. Cl. .................. 356/511; 356/446

(58) Field of Classification Search ........... 356/236, 356/625, 237.2, 237.3–237.5, 239.3, 239.8, 356/369, 446, 450, 491, 495, 511–515
See application file for complete search history.

(56) References Cited

U.S. PATENT DOCUMENTS

| | | | | |
|---|---|---|---|---|
| 4,597,665 A | * | 7/1986 | Galbraith et al. | ........ 356/239.8 |
| 4,710,642 A | * | 12/1987 | McNeil | .................. 250/559.04 |
| 5,241,369 A | * | 8/1993 | McNeil et al. | ............... 356/445 |
| 5,313,542 A | | 5/1994 | Castonguay | |
| 5,475,617 A | | 12/1995 | Castonguay | |
| 5,615,294 A | | 3/1997 | Castonguay | |
| 5,625,451 A | * | 4/1997 | Schiff et al. | ................. 356/236 |
| 5,640,246 A | | 6/1997 | Castonguay | |
| 5,729,640 A | | 3/1998 | Castonguay | |
| 5,835,217 A | * | 11/1998 | Medecki | ...................... 356/521 |
| 6,034,776 A | * | 3/2000 | Germer et al. | .............. 356/369 |
| 6,118,521 A | * | 9/2000 | Jung et al. | ..................... 356/73 |
| 6,122,047 A | * | 9/2000 | Stover et al. | ............. 356/237.3 |
| 6,573,997 B1 | | 6/2003 | Goldberg et al. | ........... 356/521 |
| 6,578,963 B2 | * | 6/2003 | Pettit | ........................... 351/212 |
| 2002/0093648 A1 | * | 7/2002 | Nikoonahad et al. | ..... 356/237.1 |

* cited by examiner

*Primary Examiner*—Samuel A. Turner
(74) *Attorney, Agent, or Firm*—Hayes Soloway P.C.

(57) ABSTRACT

A far-field measurement instrument has multiple imaging lenses cut into a pentagon shape and arranged in geodesic spherical configuration with a common field of view focused on the source of the scattered light to be measured. Aspheric lenses are used to facilitate collimation of large incident angles of scattered light. A measurement module, such as a camera, is used behind each lens. The measurement module may consist of an interferometer or Shack-Hartman wavefront sensor, thereby enabling the measurement of both intensity and phase of the scattered light.

34 Claims, 10 Drawing Sheets

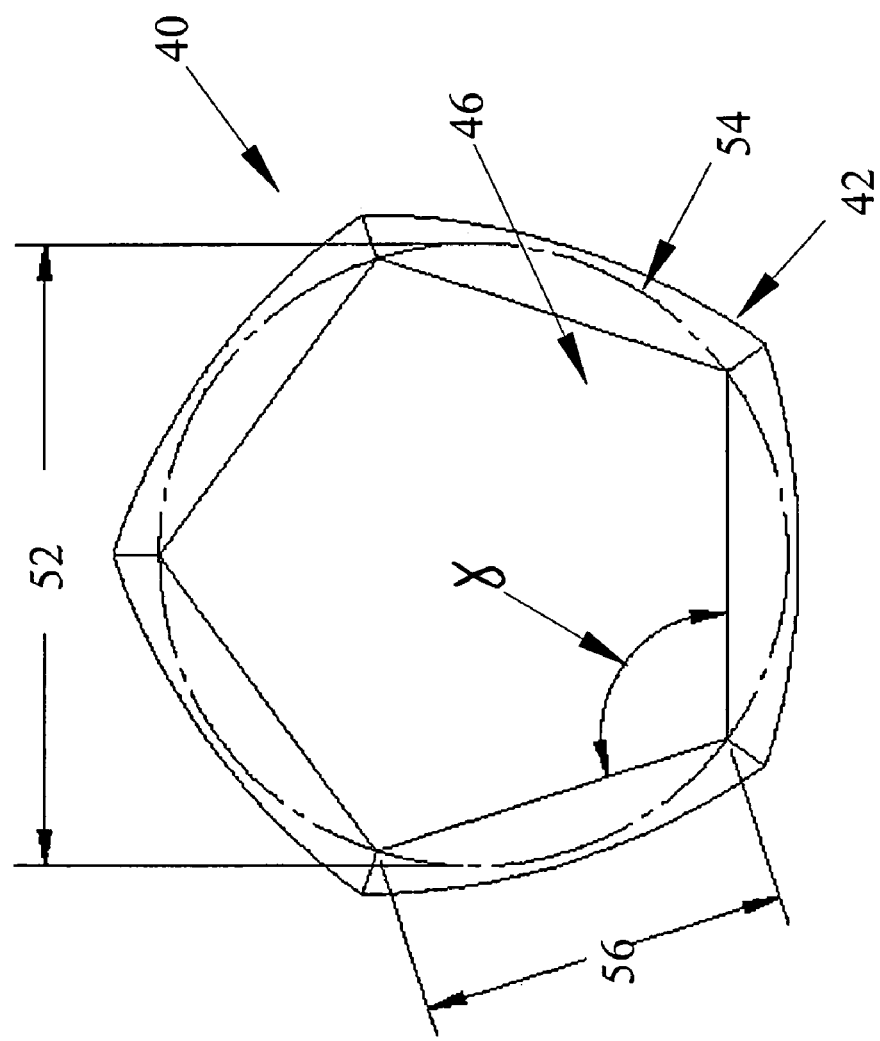
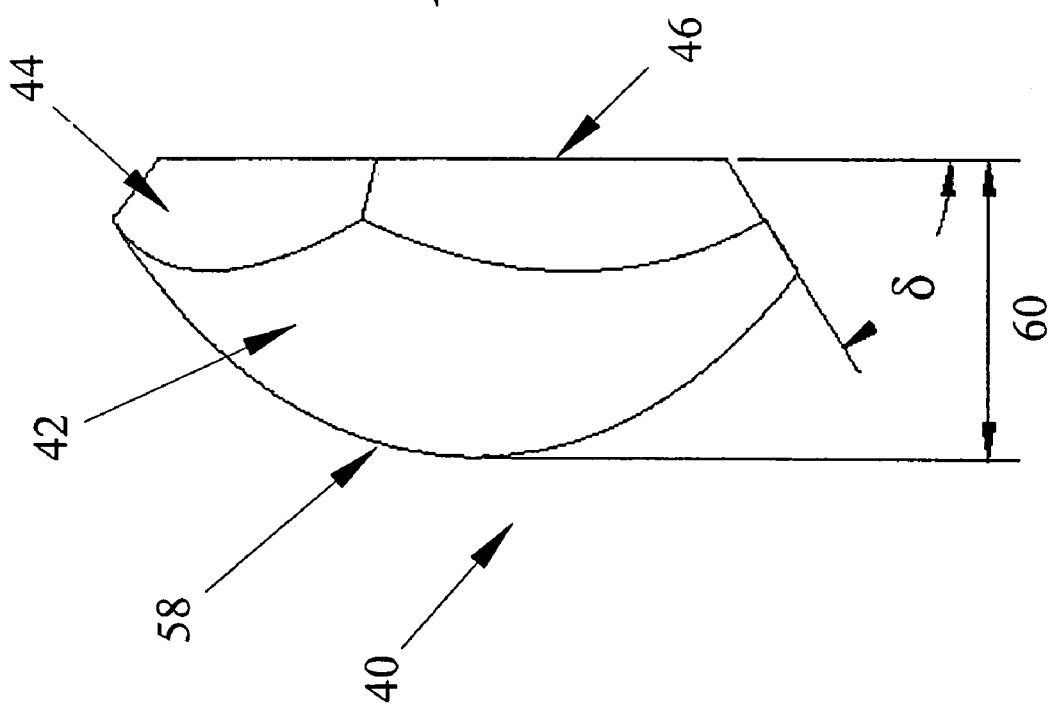
FIGURE 3B
FIGURE 3A

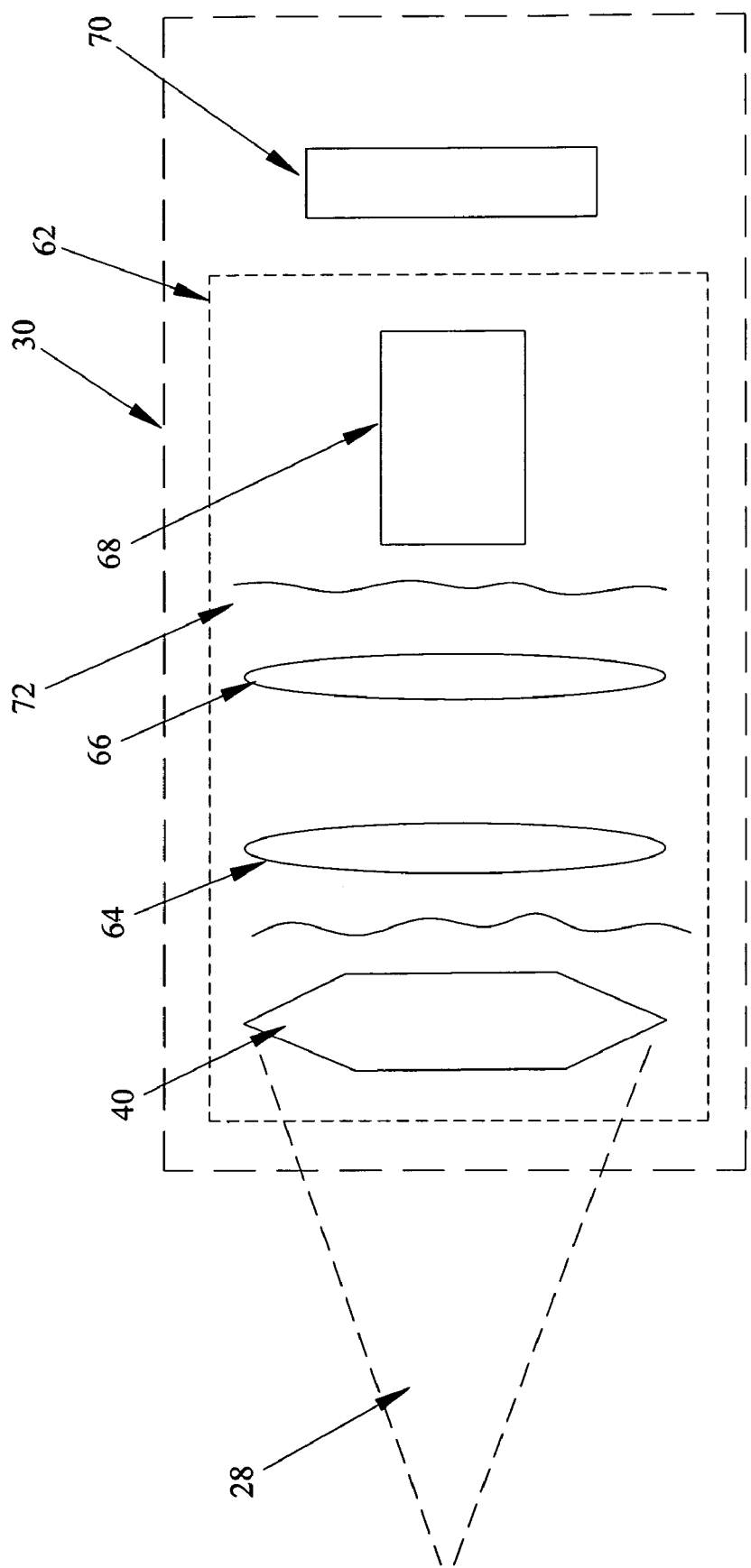

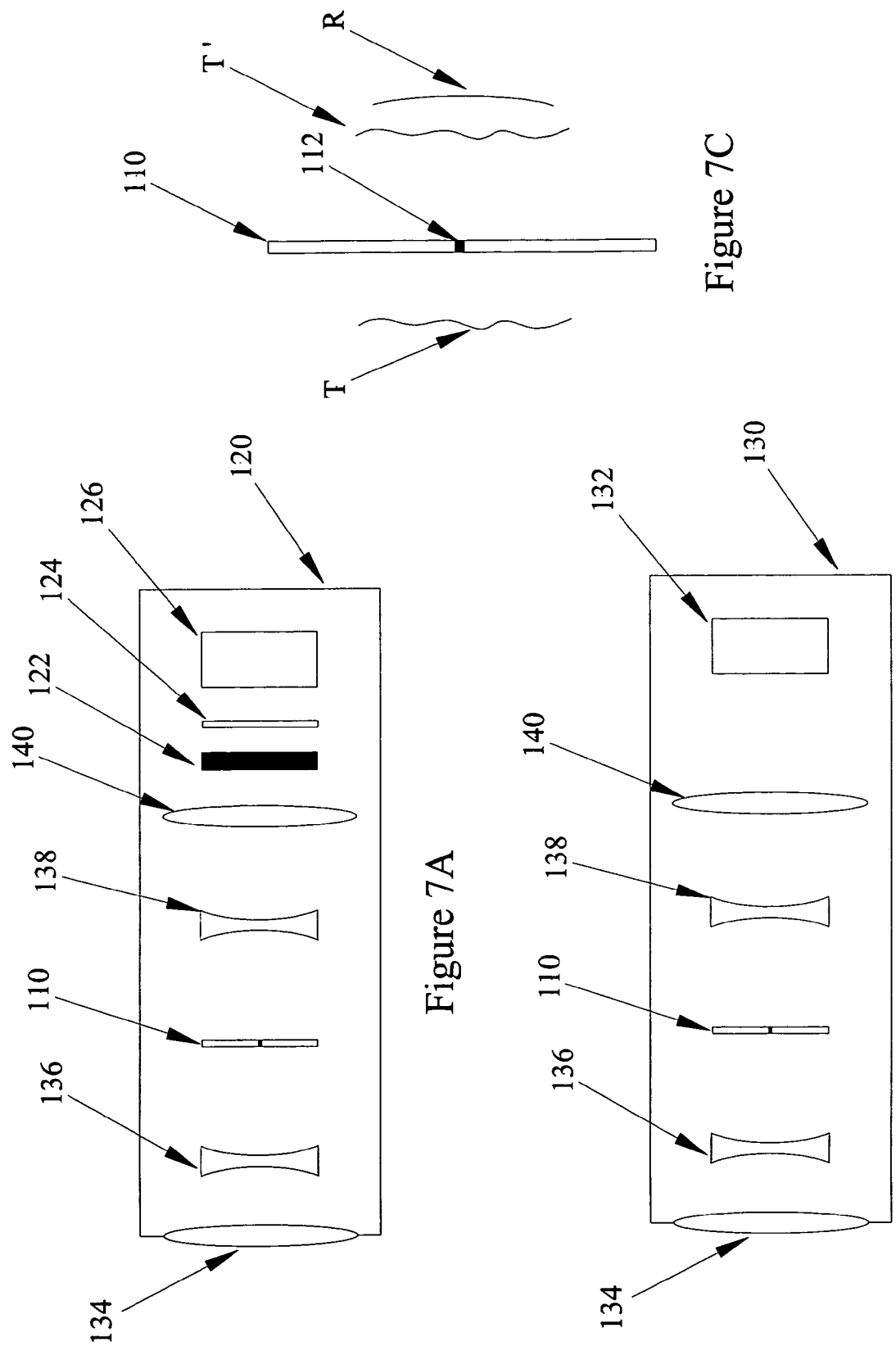

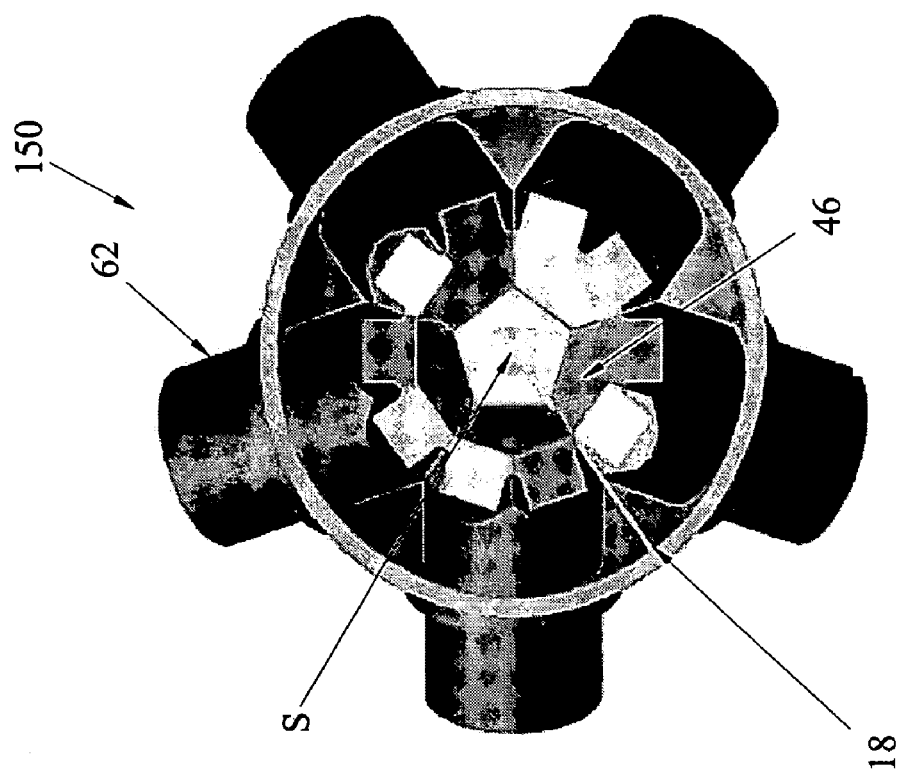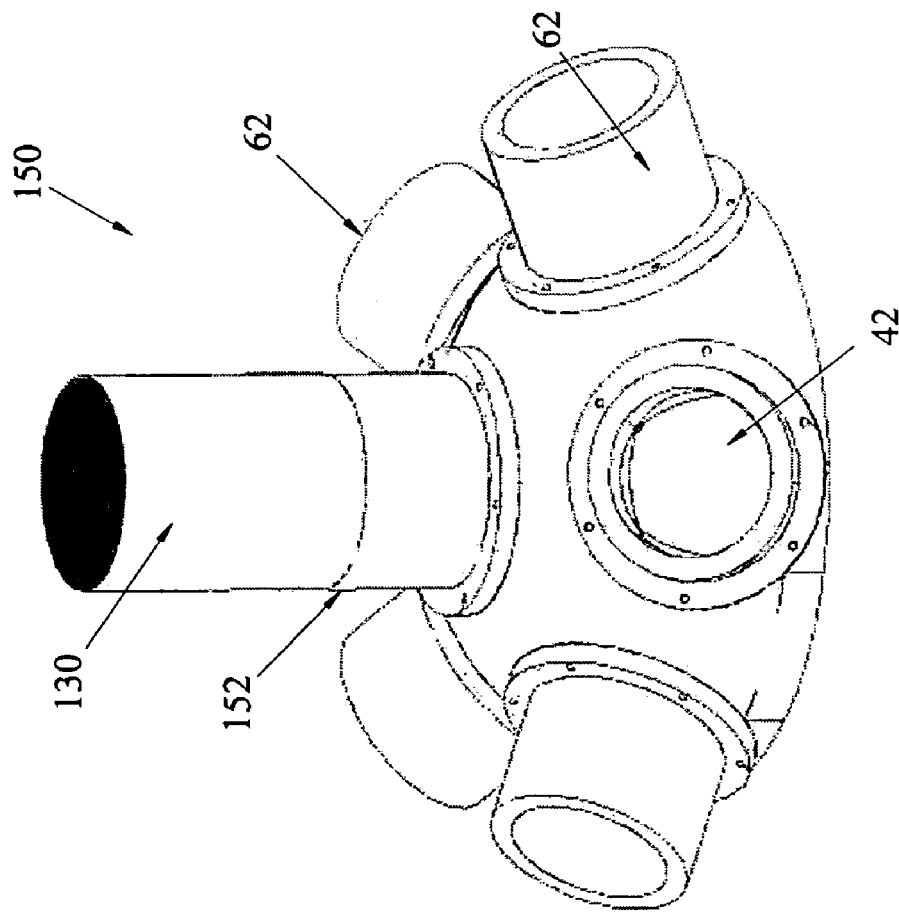
FIGURE 8B
FIGURE 8A

SPHERICAL SCATTERING-LIGHT DEVICE FOR SIMULTANEOUS PHASE AND INTENSITY MEASUREMENTS

RELATED APPLICATIONS

This application is based on U.S. Provisional Applications Ser. No. 60/450,185, filed 26 Feb. 2003, and Ser. No. 60/452,300, filed 5 Mar. 2003.

BACKGROUND OF THE INVENTION

1. Field of the Invention

The present invention relates to scatterometry. In particular, it relates to far field measurements involving the simultaneous measurement of reflected or transmitted scattered wavefronts through the use of hemispherical and/or spherical light-scatter and phase-measuring technology.

2. Description of the Related Art

Scatterometers are used to analyze light sources and material properties by measuring how a particular material or surface reflects or transmits light in spherical ("scattered") radiation. If the surface is not radiating its own light, such as in the case of an LED, a light source, such as a laser, can be directed at some angle onto the surface to produce scattered light from the point of incidence. If the surface is specular or otherwise radiates the incident light in a unidirectional fashion, all the light will be directed away from the surface along a single beam. Otherwise, the reflected light will be scattered and radiated throughout the hemisphere above the test surface. The science and mathematics of scattered light are well developed. See, for example, the book by J. C. Stover, "Optical Scattering: Measurement and Analysis," McGraw-Hill, N.Y. (1990).

A typical scatterometer includes a laser shining a beam on a test surface and a single detector that is mechanically scanned over a 180-degree circular arc around the illuminated spot. The detector's field of view is kept on the illuminated spot regardless of the viewing angle. At each view angle, a measurement is made of the light intensity, thereby generating a spatial distribution of the scattered light. The distribution over the scan arc is dependent on the characteristics of the test surface, including the type of material, surface roughness, reflectivity, color, surface structure, sub-surface damage, and others.

Scanning a single detector has greatly limited the ability to measure scattering over large areas, such as over an entire hemisphere, and to measure large dynamic ranges of intensity. Moreover, scanning over an entire hemisphere takes a lot of time. Thus, measuring scattering over many spots on the test surface has been quite impractical with a single detector. Measuring dynamic events at multiple measurement positions has also not been possible with this approach.

In order to overcome these limitations, multiple detectors with a single detecting element distributed over a larger hemispherical area have been used. For example, a limited number of detectors (from 10 to 120 detectors) have been placed along an arc, where the arc center is the measurement point. This approach works well when the scatter field (or far-field pattern, as defined herein) is uniform, but it does not work when the far field pattern is random or has a high frequency content.

Another prior-art approach is to shine a laser beam through a hole in a translucent dome onto a test sample positioned at the center of the dome. The scattered light from the test sample illuminates the interior dome surface, which, because it is translucent, permits the use of a camera to view the scattered light from the dome's exterior face. This approach works satisfactorily for some basic applications. However, the light can also scatter laterally between the dome's interior and exterior surfaces producing corrupted measurement results. This method also does not allow for easy measurement of the light scattered at angles approaching 90 degrees from the direction normal to the surface of the camera (i.e., the hemispherical dome's edge).

Another method for hemispherical scattered-light measurements is described in U.S. Pat. No. 5,313,542, U.S. Pat. No. 5,475,617, U.S. Pat. No. 5,615,294, U.S. Pat. No. 5,640,246, and U.S. Pat. No. 5,729,640. This approach is based on the use of a fiber-optic bundle to measure a portion of the hemisphere in three dimensions. This is done by cutting a spherical surface onto a tapered portion of a fiber bundle. The opposite end of the fiber bundle is tapered to a much smaller size for coupling to a camera. This method allows very high-resolution measurements over a portion of the hemisphere. However, its main disadvantages are a lower dynamic range, the expense of the fiber bundles, the loss of phase information as the light travels though the fiber, and the mechanical scanning requirements for full hemispherical measurements.

Thus, all of these prior-art methods have common limitations in the degree of far-field coverage and angular measurement resolution. In addition, they cannot measure phase. Therefore, a system capable of measuring both spherical scatter and phase with a single instrument in real-time would be very desirable in the art and would provide unprecedented medical diagnostic capability. The present invention provides a solution to many of the problems of the prior-art devices and enables the acquisition of significantly more measurement data at speeds not possible before. Moreover, both spherical and phase information from scattered light can be acquired simultaneously.

SUMMARY OF THE INVENTION

The present invention utilizes a unique lens design to image the light emanating from a sample source onto a set of measurement modules adapted to measure intensity and phase. As a result, the invention makes it possible to measure scattered or radiated light with high resolution over a hemisphere or a full sphere collected from a light source positioned at the center of the sphere. The resulting measurement produces an image similar to that seen in three dimensions by a human eye observing the light source from a 360-degree vantage point, all at high resolution and at one time. In addition, phase can also be simultaneously measured, thereby providing data that can be used advantageously to reveal significant material properties not available with intensity measurements alone.

According to one aspect of the invention, the preferred embodiment consists of a far-field measurement instrument that has multiple imaging lenses cut into a pentagon shape and arranged in a geodesic spherical configuration. The pentagon shape allows the lenses to fit together in a geodesic dome pattern where all the lenses have a common field of view substantially focused on the source of the light to be measured. This lens configuration allows the collection of all light irradiating radially from a point source, thereby providing a substantial advantage over the prior art, which utilized round collection optics that produce dead zones over the measurement region. Other non-circular shaped lenses are possible, but it has been determined that a pentagon shape gives the optimum balance of image quality, number of lenses, dome size, and far-field measurement coverage. All lenses have a common field of view, which, if the lenses are disposed in substantially hemispherical or spherical configuration, is the center of the corresponding geodesic dome.

In order to reduce the number of lenses required to create a spherical structure, each lens must be quite large, which causes significant aberrations in the wavefront. Thus, according to another aspect of the invention, each pentagonal imaging lens consists of multi-element optics designed to reduce wavefront aberration. For example, such optics may consist of a typical zoom lens wherein the first sub-element is an aspheric pentagon-shaped lens. As is well understood in the art, the aspheric design allows for large incident angles of scattered light while minimizing the number of sub-lenses required to correct for aberrations. A fresnel lens that simulates the aspheric design can be used instead of the aspheric lens. Fresnel lenses produce images of lower quality, but they are substantially thinner and lighter. Therefore, either an aspheric or a fresnel lens could be used to practice the invention depending on the requirements of the actual application. Behind the pentagon-shaped lens, additional sub-lenses are used to collimate and flatten the wavefront in preparation for imaging it into a camera inside the measurement module. In the preferred embodiment, each module includes an aspheric pentagon-shaped lens, a collimator lens, a field-flattener lens, and a module imaging lens. A single-element pentagon shaped lens can be used for less demanding applications.

A measurement module, such as a camera, is used behind each multi-element lens. According to a particular embodiment of the invention, the measurement module consists of a Shack-Hartman wavefront sensor, thereby enabling the measurement of both intensity and phase of the detected wavefront. In another embodiment, the measurement module is an interferometer that requires the incoming wavefront to be phase-shifted with respect to an external reference wavefront. The preferred version of this embodiment includes a point diffraction interferometer in each measurement module. The point diffraction interferometer creates its own reference beam from the far-field wavefront, thus both intensity and phase can be measured. Other types of interferometers can also be used including a shearing interferometer.

Each measurement module interfaces in conventional manner with a computer that processes the information and preferably also displays the results. Dynamic events can be captured by electronically synchronizing each of the measurement modules for simultaneous data acquisition. Due to the large amount of information, a video or DVD recorder can be used to record the data in real time for analysis at a later time. It is also expected that neural networks will play a major role in processing the raw data acquired from the measurement modules of the invention. The resulting data can be used to characterize many materials and substances, including smooth and rough surfaces, semiconductors, airborne particles, biomaterial, gases, liquids, and molecular structures.

Various other purposes and advantages of the invention will become clear from its description in the specification that follows and from the novel features particularly pointed out in the appended claims. However, such drawings and description disclose only some of the various ways in which the invention may be practiced.

BRIEF DESCRIPTION OF THE DRAWINGS

FIG. 3A is a side view of a pentagon-shaped lens according to the invention.

FIG. 3B is a front view of the pentagon-shaped lens of FIG. 3A.

FIG. 5 is a schematic illustration of a measurement module with a multi-element lens and a camera.

FIG. 7A is a schematic representation of a point-diffraction interferometer suitable for practicing the invention wherein a crystal retarder is used for phase shifting.

FIG. 7B is a schematic representation of another point-diffraction interferometer with simultaneous phase shifting.

FIG. 7C illustrates a point-diffraction interferometer element for generating a reference wavefront from a test wavefront.

FIG. 8A is a perspective view of a hemisphere structure including the multiple measurement modules of the invention.

FIG. 8B is a bottom view of the structure of FIG. 8A illustrating the hemispherical geodesic configuration of the pentagonal lenses of the invention.

DETAILED DESCRIPTION OF THE INVENTION

The invention lies in the combination of a system of aspheric lenses with a corresponding system of light detectors arranged in contiguous configuration so as to simultaneously capture and measure all the light scattered from a point source on a sample. Moreover, with the use of appropriate detectors, the phase distribution of the scattered light can be similarly measured.

As used herein, the terms "far field pattern" and "scattered light" are used interchangeably to refer to light radiating in a radial pattern from a point light source. The terms "spherical" and "hemispherical" are used to refer to such geometrical shapes as well as to portions thereof having a spherical geometry (i.e., the geometry of figures on a sphere). "Equatorial plane" is defined as the plane that is coplanar with the equator of a structure having such spherical geometry. Finally, the term "geodesic" is used to refer to a polyhedral structure having plane faces connected to one another which also are preferably, but not necessarily, configured so that the sides of each face defines the shortest line between points of a given surface, such as a hemisphere.

Figure 1B:
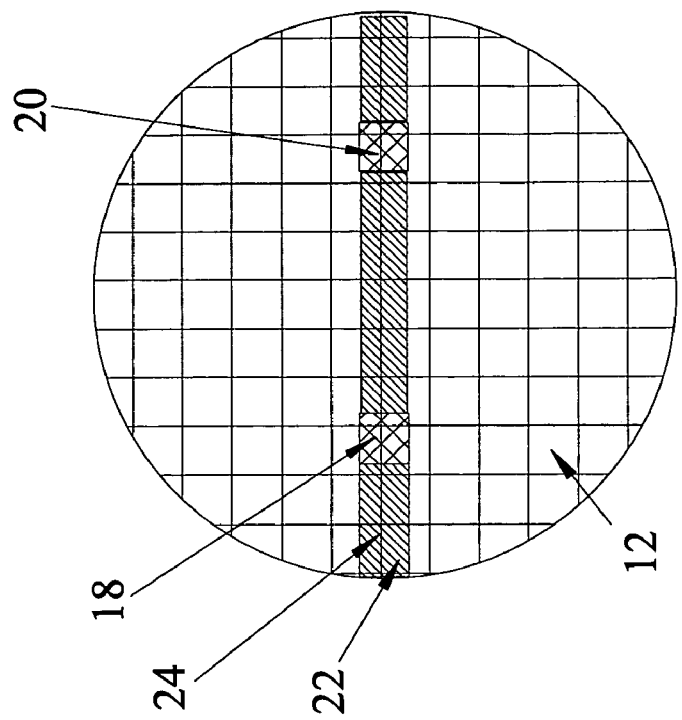
FIG. 1B is a schematic top view of the dome of FIG. 1A.
Figure 1A:
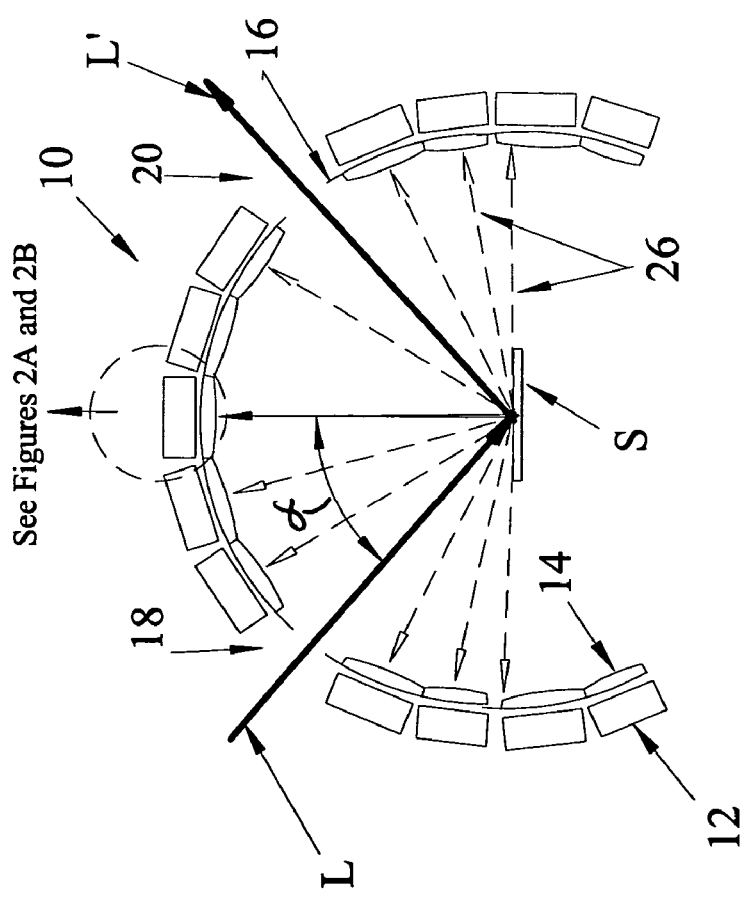
FIG. 1A is a schematic sectioned side view of a substantially hemispherical dome covered internally with measurement modules according to the invention.

Referring to the drawings, FIGS. 1A and 1B illustrate the invention in a substantially hemispherical configuration 10 shown in sectioned and top views, respectively. Measurement modules 12 and corresponding lenses 14 are connected to a hemispherical support structure 16 so as to provide nearly full coverage of the hemispherical surface. While pentagon-shaped lenses and corresponding measurement modules are preferred to practice the invention, as described above, small square elements are used in these figures for purposes of illustration. In fact, it is clearly understood that the spherical curvature of the structure 16 would require each module and lens 12,14 to depart from a true square geometry in order to cover the structure 16 without gaps. This design of FIG. 1A would require a large number of lenses 14, which would produce high-resolution measurements but at a prohibitive cost because of the correspondingly large number of modules 12.

A beam of light L, such as produced by a laser source (not shown), can be projected through an aperture 18 in the hemisphere structure 16 toward a test sample S at a desired angle $\alpha$. The angle $\alpha$ can be between zero and ninety degrees with respect to the normal to the sample surface. The beam L could also be generated from a small light source inside the hemisphere of the invention. If the sample surface S is partially specular, a portion of the light L is reflected off the surface and directed outward through a second aperture 20 in the hemispherical structure 16. In order to ensure that the reflected beam passes through the aperture 20 and is projected outwardly, a manual or motorized stage 22 is provided (shown schematically in FIG. 1B) to change the angle $\alpha$ appropriately. This feature is important for those measurements where it is undesirable for the beam L to reflect off of the lenses 14 back towards the sample surface S. Alternatively, a narrow long slit cut into hemispherical structure 16 along a line 24 lying in the plane of reflection of the beam L could be used to allow the beam L to enter at any desired angle and yet ensure its departure from the structure. If the sample surface S is non-specular, the aperture 20 and stage are optional because all light L is scattered inside the hemispherical structure. In such a case, an additional measurement module may be used in place of the aperture 20.

Figure 2B:
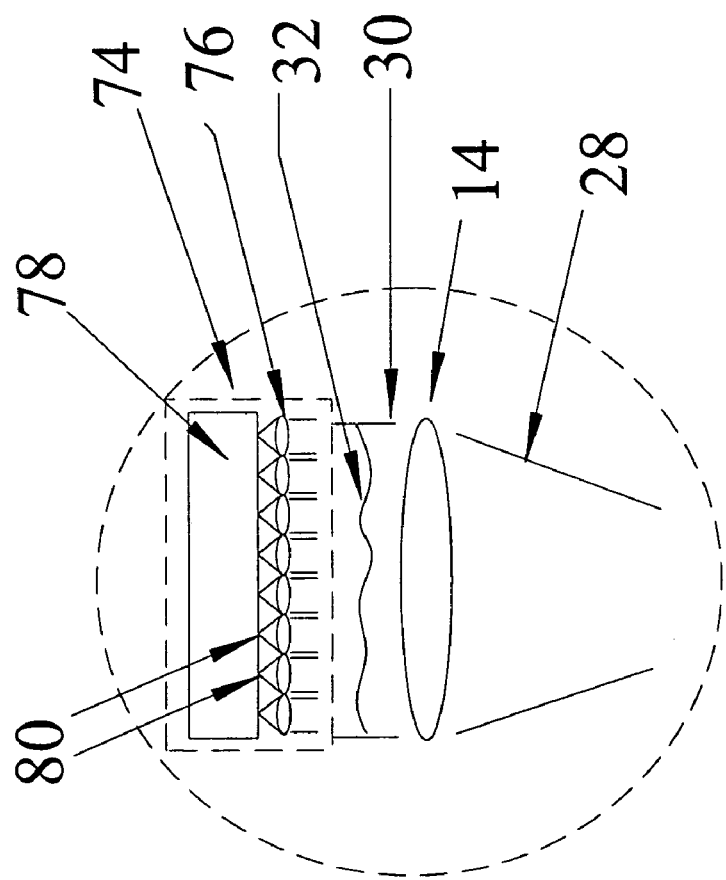
FIG. 2B is an enlarged schematic view of far-field light imaged on a Shack-Hartman wavefront sensor.
Figure 2A:
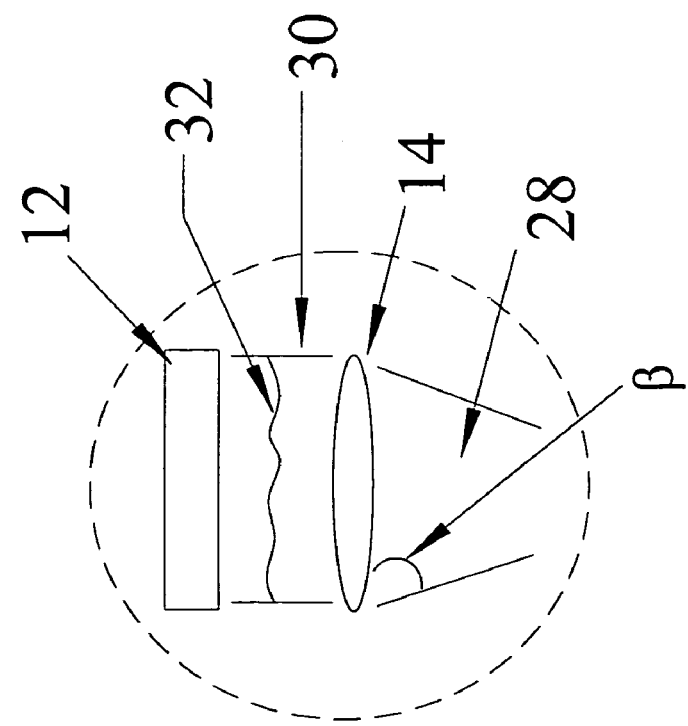
FIG. 2A is an enlarged schematic view illustrating far-field light imaged on a measurement module.

In either case, the beam L scatters off the sample surface S in radial fashion towards the system of lenses 14, as illustrated by the arrows 26 in FIG. 1A. According to the invention, all of this scattered light is collected simultaneously for data analysis using the system of lenses 14. As shown in FIGS. 2A and 2B, a portion 28 of the far-field pattern radiated from the sample surface passes through each lens 14. The purpose of the lens 14 is to collimate and flatten the spherical far-field pattern 28. The resulting processed far-field pattern or wavefront 30 is then directed into a measurement module 12, which can be a camera for measuring intensity or an interferometer for measuring intensity and phase. FIG. 2B illustrates the module 12 in the form of a Shack-Hartman wavefront sensor for measuring intensity and phase.

The lens 14 may be a single- or multi-element lens. As one skilled in the art would readily recognize, the quality of the wavefront 32 directed to the measurement module 12 will depend on lens 14. If the lens is small, it can be implemented as a single-element lens to achieve a high-quality wavefront, but many measurement modules are required, which can be expensive and impractical. If the lens 14 is large, fewer measurement modules are required but high wavefront quality is difficult to achieve because of the large incident angle $\beta$ of the scattered light at the edge of the lens 14. Also, virtually all conventional lenses are circular in shape. Therefore, if conventional round lenses are placed side by side in a checkerboard pattern, many missing gaps remain that result in missing information. Therefore, the invention is preferably implemented using a lens design selected to achieve a judicious balance between the number of lenses 14, the lens-shape complexity, and the quality of the wavefront 32.

Figure 4B:
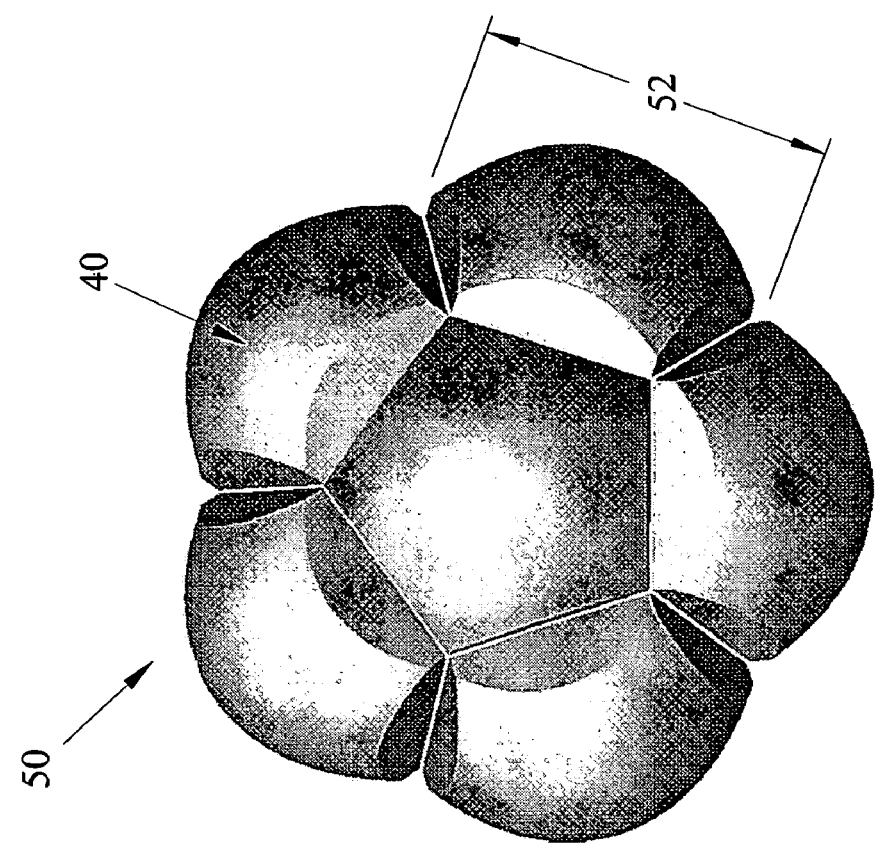
FIG. 4B is a top view of the structure of FIG. 4A.
Figure 4A:
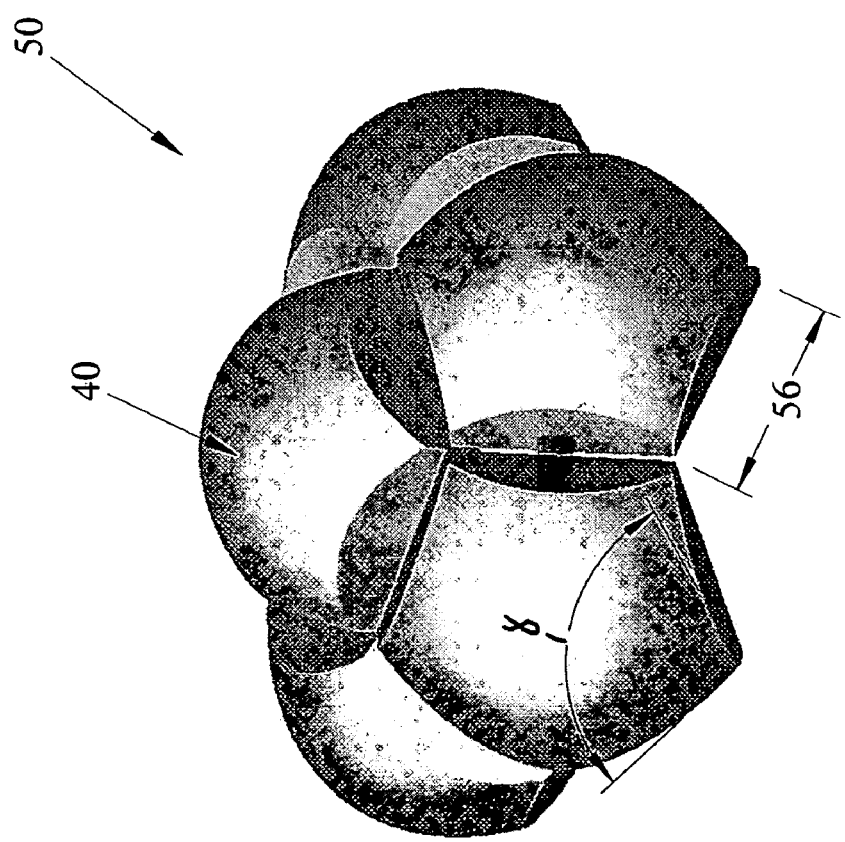
FIG. 4A is a perspective view of a substantially hemispherical dome composed of six pentagon-shaped lenses as illustrated in FIG. 3B.

FIGS. 3A and 3B illustrate a pentagon shaped lens 40 according to the invention in side and front view, respectively. A round lens 42 is cut into a pentagon shape by making five precision cuts 44 around the lens. In a pentagon, the angle $\gamma$ (FIG. 3B) between sides is 108 degrees. In the preferred embodiment, the angle $\delta$ (FIG. 3A) of each cut 44 with respect to the pentagonal face 46 is adjusted to about 58.3 degrees to allow for the easy manufacture and fitting of multiple lenses together. Using six pentagon lenses 40, a geodesic dome 50 can be constructed, as illustrated in FIGS. 4A and 4B. Depending on the diameter 52 of the circle 54 that includes the pentagonal face 46 of the lens 40, different size domes can be generated. In the preferred embodiment, the lens 40 has a diameter 52 of 78.94 mm and a pentagon side 56 of 40.43 mm. These dimensions produce a dome 50 (FIG. 4B) of approximately 264.8 mm in diameter.

Although the lens 40 can be of various types, the preferred embodiment of the invention utilizes an aspheric design. This allows the lens 40 to be quite large and still measure scattered light incident at large angles $\beta$ (see FIG. 2A). As is well understood in the art, the exact shapes of the surface 58 of the lens 40 and the pentagonal surface 46 are critical factors in the design of an aspheric lens because the quality of these two surfaces governs the overall performance of the lens and the quality of the final far-field measurement.

A typical aspheric lens design is governed by the following equations:

Curvature=$c$=1/$R$, and $$SAG=Z=(c*r^2)/(1+(1-(1+k)c^2 r^2)^{1/2})+a_2 r^2+a_4 r^4+a_6 r^6+a_8 r^8+\ldots+a_n r^n$$

where $c$ is the curvature, $R$ is the radius, $Z$ is the sagittal height, $a_n$ are constants, and $r^n$ are radial values. The aspheric surfaces 46 and 58 can be of various shapes depending on the acceptable wavefront quality. In the preferred embodiment, the surface 46 is flat and the equation parameters for the aspheric surface 58 are as follows:

$R = 35.1657$
$k = -0.9532$
$a_2 = 0$
$a_4 = 1.2065\text{E}-6$
$a_6 = 1.7981\text{E}-10$
$a_8 = 4.86192\text{E}-14$
$a_{10} = -2.9165\text{E}-18$ Using these equation parameters, the height 60 of the aspheric lens 40 is 33 mm.

Another advantage of an aspheric lens is that it affords a significant reduction in the number of sub-elements required in a multi-element lens design. For example, a multi-element lens 62, as illustrated in FIG. 5, can employ sub-element lenses to reduce aberrations introduced into the far-field pattern by the aspheric lens 40. This is important because it makes it possible to minimize the error in the final far-field measurement. There are various lens sub-elements that can perform this task. In the preferred embodiment of the invention, three additional lenses are used. As shown in FIG. 5, a collimator 64, a field flattener 66, and an imaging lens 68 are used. The imaging lens 68 may itself also be a multi-element lens. Thus, a far-field pattern 28 would enter lens 40 and travel through lenses 64, 66, and 68 before reaching the measurement module 70. The module 70 can be a camera for intensity measurements, an interferometer for phase and intensity measurements, or a Shack-Hartman wavefront sensor for phase and intensity measurements. The ability to measure both phase and intensity of a far-field pattern over a hemisphere represents a significant advance in the art of scatterometry.

Thus, in addition to measuring intensity (represented by wavefront 30 in FIG. 2A), the invention can be implemented to also measure the phase of the wavefront (represented by wavefront 32 in FIG. 2A). This may be accomplished by using an interferometer, as illustrated by the module 12 of FIG. 2A, or a Shack-Hartman sensor 74, as shown in FIG. 2B. As illustrated in that figure, the Shack-Hartman sensor utilizes a micro-lens array 76 to focus the collimated light 30 onto a camera 78. The lens 14 is optional and is used to collimate the far-field pattern 28 onto the micro-lens array 76. Generally, N×N camera pixels are mapped by each micro lens. Thus, the exact pixel position of the focused spots 80 in this grid of camera pixels can be used to determine phase. For the implementation of this invention, 15×15 camera pixels per micro lens are preferred. It is noted that the use of Shack-Hartman sensor enables the dual acquisition of phase and intensity information from both the reflected beam L' and the scattered light 26 illustrated in FIG. 1A.

Figure 6B:
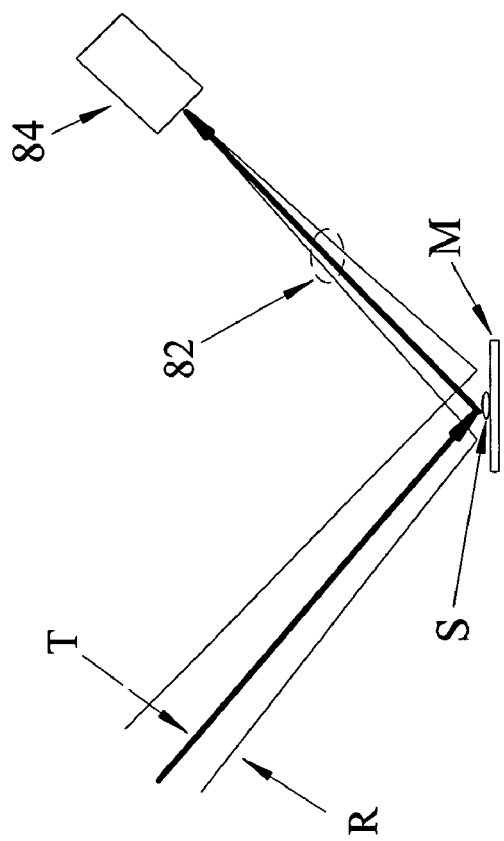
FIG. 6B illustrates the operation of the interferometric device of FIG. 6A.
Figure 6A:
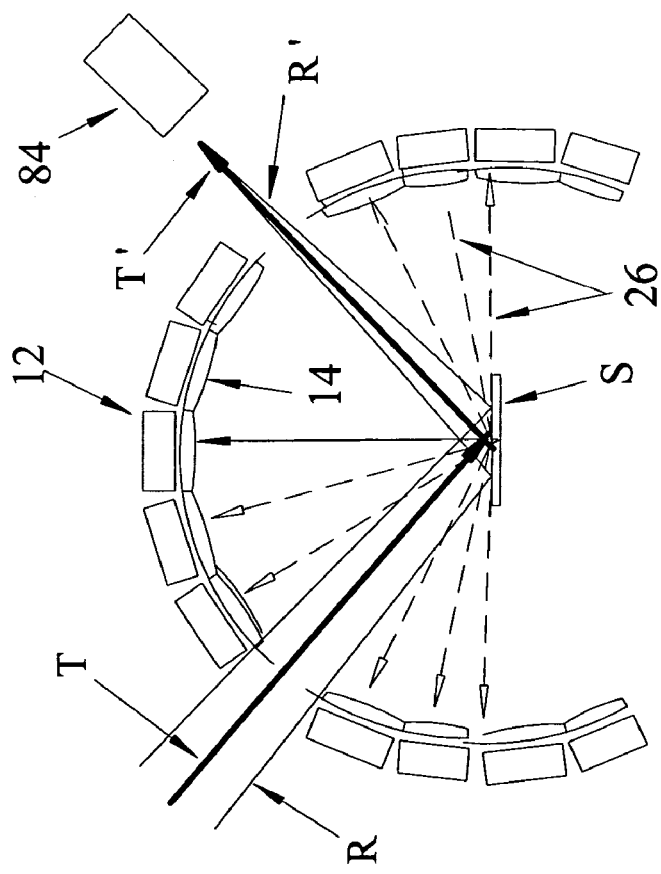
FIG. 6A is a view of the dome of FIG. 1A illustrating scattering of a light injected into the dome for imaging according to the invention and including a device for measuring phase using interferometric methods.

As illustrated in FIGS. 6A and 6B, phase can also be measured using an interferometric set up affecting the input light introduced to the hemispheric dome of the invention. A relatively wide converging reference beam R and a relatively narrow test beam T are projected together onto a polished reference surface M and a smaller overlaying test sample S, respectively. For the purposes of this disclosure, the surfaces M and S are considered substantially coextensive. Thus, the two beams R,T produce an interference pattern in the region 82 where they overlap after reflection from the test and reference surfaces, and the pattern may be imaged and measured by an interferometric sensor 84. By temporally phase shifting the reference beam R with respect to the test beam T, a series of interferograms is provided as needed for conventional phase analysis. For example, FIGS. 6C and 6D illustrate two approaches suitable to produce and phase shift reference and test beams used to illuminate a sample surface in the scatterometer of FIG. 1A.

Figure 6D:
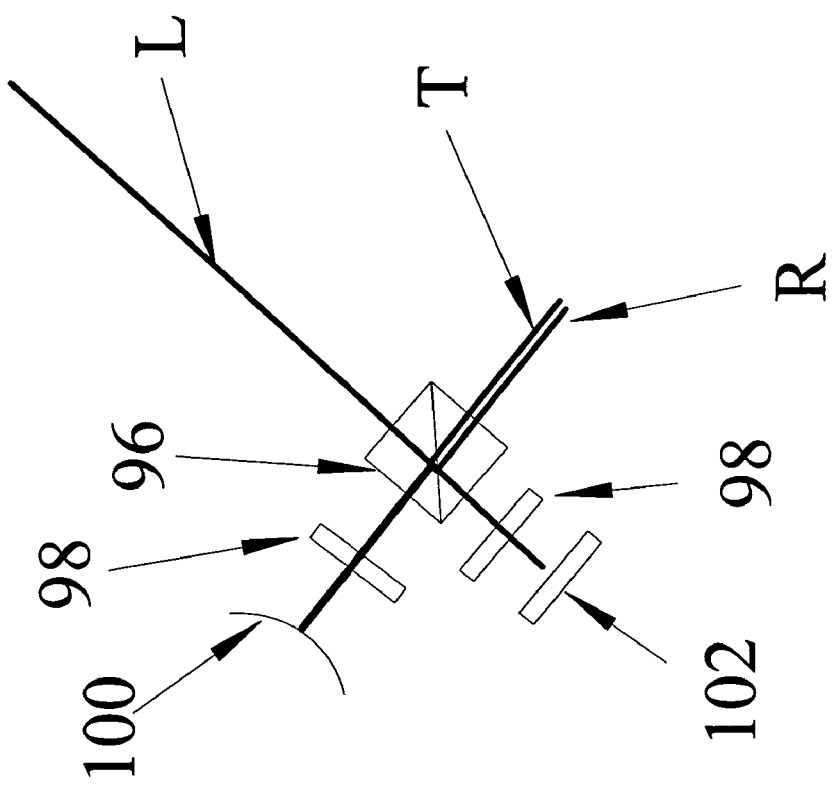
FIG. 6D is a schematic illustration of a polarization interferometric device designed to provide collinear test and reference beams converging at different rates.
Figure 6C:
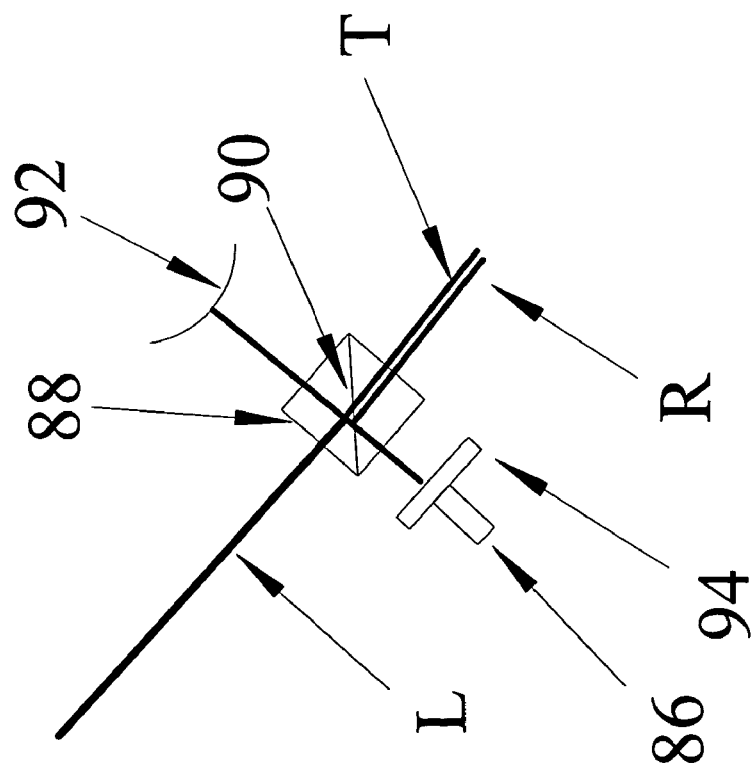
FIG. 6C is a schematic illustration of a piezoelectric interferometric device designed to provide collinear test and reference beams converging at different rates.

The phase-shifting device of FIG. 6C utilizes a conventional piezoelectric element 86. A converging laser light beam L (the source is not shown in the figures) is split into a test beam T and a reference beam R through a non-polarizing beam splitter 88. The test beam T consists of the original beam L passed through the splitter and directed toward the test sample S (see FIG. 6B). The reference beam R is produced by reflecting the beam L off the splitter surface 90 toward a convex mirror 92, which reflects the light back through the beam splitter and onto a mirror 94 operatively connected to the piezoelectric element 86. The convex mirror 92 is used to reduce the convergence rate of the laser beam L, such that the resulting reference beam R is bigger than the test beam T at the test sample S (as shown in FIG. 6B). The light R is reflected by the mirror 94, recombined with the test beam T passed the beam splitter 88, and then phase shifted by applying a voltage to the piezoelectric element 86 attached to mirror 94. The convex curvature of the mirror 92 provides the reduced convergence needed for the reference beam R to shine over the reference surface M, as illustrated in FIG. 6B. This unique design allows the smooth reference surface M to be placed under the test sample S in the same optical path of both the test and reference beams T,R. The reference beam R is made larger to ensure its reflection from the reference mirror M.

Phase shifting can also be performed in a solid-state mode by making the reference and test beams orthogonally polarized, as shown in FIG. 6D. A polarizing beam-splitter 96 is used to split the incoming beam L into linear orthogonally polarized test and reference beams T,R. Quarter-wave plates 98 are used along the path of each beam to convert the linear polarized light to circular polarized light as the beams travel toward respective mirrors 100 and 102. As the reflected beams travel back from these mirrors through their respective wave plate, they are converted back to linear polarized light rotated 90 degrees with respect to their initial linear polarization, so that the two beams may be appropriately directed toward the sample object by the splitter 96. The recombined beams are then reflected by the reference and test surfaces M,S, as shown in FIG. 6B. A polarization phase-shifting interferometer is then used in the interferometric sensor 84 to convert in conventional manner the two beams into three or more phase-shifted interferograms for analysis.

Using either interferometric approach with the scatterometer of FIG. 6A, the reflected beams T', R' are intentionally caused to travel outside the dome to reach the interferometric sensor 84 in order to minimize the effect of scattered light returning from the sensor back to the surface M, which would cause measurement errors. The method of FIG. 6A is limited by the fact that the modules 12 around the dome are cameras while the module 84 is an interferometer. Thus, the phase measurements cannot be made over the entire far-field pattern. Moreover, having the test and reference surfaces S, M located at the same location is impractical for many applications. The use of mechanical piezoelectric devices also introduces limitations due to vibrations, changes in the environment, and changes in the test sample over time. Similarly, the interferometric method of FIG. 6D assumes that the polarization states of the beams R and T are not changed randomly due to the scattering properties of the surfaces S and M. This assumption cannot be made for a variety of surfaces and materials. In addition, both of these interferometric methods would not work if the sample object S were a self-illuminating source. Finally, although the Shack-Hartman approach of FIG. 2B has fewer of these limitations, it suffers from a lower angular measurement resolution than interferometric methods.

Due to these limitations, a point-diffraction interferometric approach is preferred, as illustrated schematically in FIGS. 7A and 7B. A point-diffraction interferometer generates its own reference wavefront R from a test wavefront T, as shown in FIG. 7C. The test wavefront T passes through a quarter-wave plate 110 with a pinhole 112. The portion T' of the wavefront T that passes through the wave plate 110 has its polarization rotated 90 degrees. The portion of the wavefront T that passes through pinhole 112 is converted to a spherical wavefront R while maintaining its original polarization state. Thus, the two altered wavefronts T' and R create an interference pattern that can be processed to recover the original test far-field phase pattern of the beam T.

Two types of point-diffraction interferometers can be used. The interferometer 120 illustrated in FIG. 7A uses a crystal retarder 122 and linear polarizer 124 to phase shift the reference wavefront R with respect to the test wavefront T'. The resulting phase-shifted interference images are imaged onto a camera 126. The interferometer 130 of FIG. 7B utilizes a polarization-based simultaneous phase-shifting module 132 to perform the same function. In both interferometers 120 and 130, lenses 134, 136, 138, and 140 are used to image the wavefronts correctly to the measurement modules 126 and 132.

FIGS. 8A and 8B illustrate a dome structure 150 constructed according to the invention with six measurement ports 152. In the preferred embodiment, each port has a multi-element lens (of the type 62 illustrated in FIG. 5) and an interferometric module (of the type 130 illustrated in FIG. 7B). For simplicity of illustration, only one port 152 is shown with the completed lens and measurement modules 62 and 130. The six pentagonal aspheric lenses 40 are seen in the bottom view of dome 150 shown in FIG. 8B. It is noted that two mirror copies of the dome 150 can be combined to create a complete sphere for measuring far-field patterns over a full 360-degree range in three dimensions. This embodiment of the invention is preferred when the test sample S is transmissive or when it radiates light over a full sphere. Otherwise, only one dome 150 is required to practice scatterometry as taught by the invention.

The advantages of measuring a full sphere of intensity and phase information include the ability to measure complete three-dimensional radiated light from translucent materials for applications such as DNA analysis, bio-matter, polymers, plastics, and more. Furthermore, all measurements can be done in real-time for monitoring dynamic events.

Irrespective of the particular lens design, various methods can be used to mount the measurement modules into a spherical structure. For example, with reference to the module of FIG. 2A, holes in the spherical structure may be used to mount a module 12 in each hole. Alternatively, a glass hemispherical or spherical structure can be used as a mold for placing and bonding lenses 14 and sensor modules 12. The mold may or may not be removed after lens placement. The lenses can have various shapes. However, when lens 14 is a single-element lens in this design, a simple solution is to have bio-convex lenses with the back-face curvature matching the sphere and the front-face curvature designed to collimate the light radiating from the sphere's center.

Another, preferred approach when the lenses 14 consist of a single-element lenses is to use a single monolithic macro-lens array in the shape of a hemisphere or sphere. Such a structure can be glass, plastic, or other material suitable for lens arrays. In all cases an antireflective coating can be used on the lens surfaces. In all cases the measurement system may be for measuring intensity and/or phase.

Thus, it has been shown that the invention provides an instrument that is suitable for measuring far-field patterns of scattered light over an entire sphere. In addition, the instrument can measure such scattered light with high resolution without any gaps (blind spots) in both hemispherical or spherical configurations with acceptable distortions of the scattered field. Finally, both light intensity and phase may be measured in the far-field pattern over an entire sphere.

Figure 9B:
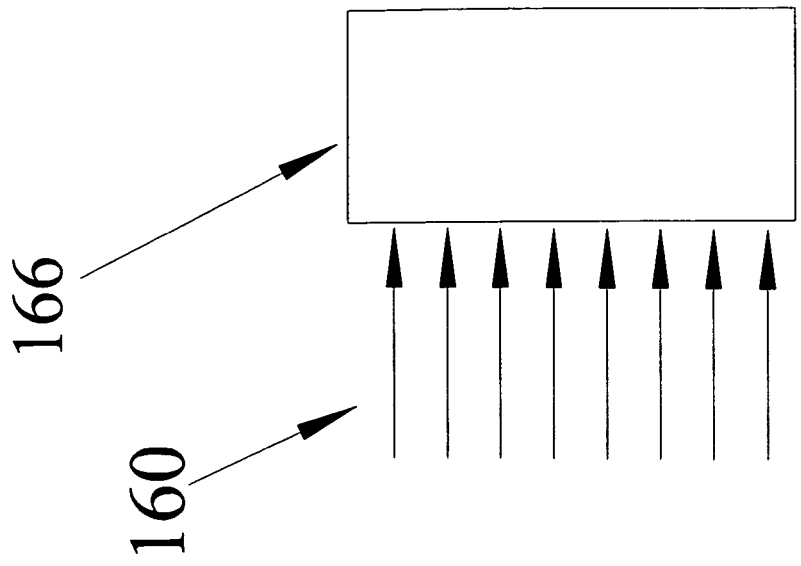
FIG. 9B illustrates schematically a configuration for interfacing the camera(s) in a measurement module to a video recorder.
Figure 9A:
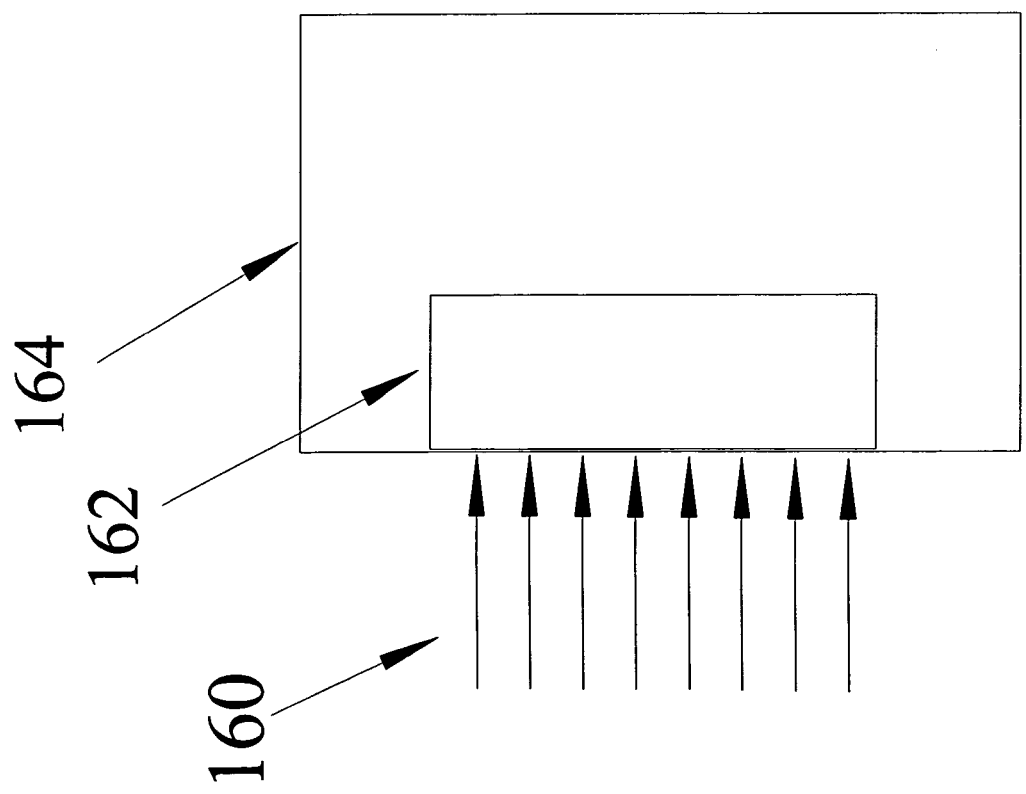
FIG. 9A illustrates schematically a configuration for interfacing camera(s) in a measurement module to an image processor and computer.

As illustrated schematically in FIG. 9A, the measured data from the cameras inside the detector modules 12 or 78 (see FIGS. 2A and 2B) are converted to electrical signals 160 and sent to a processor 162 in a conventional computer 164 for interferometric analysis. Alternatively, as shown in FIG. 9B, the electrical signals 160 can be sent to a video or DVD recorder 166. The cameras inside modules 12 and 78 may be synchronized to view the same event at the same time. This feature represents a significant advantage when measuring dynamic events and is the preferred mode of operation. Another advantage of multiple cameras is the fact that each camera can have its own separate automatic shutter and exposure settings. This allows simultaneous acquisition of high intensity light (near the reflected beam) and low-level light where light scatter is minimal.

Also importantly, it can be seen from FIG. 1A that the power of the light source producing the beam L can be controlled to allow a broad range of bright and dim regions of scattered light to be measured. The power of the source can be lowered to allow modules of the invention to view bright regions of scattered light, and then the power can be increased to allow dimmer regions of scattered light to be measured by the modules. Another significant advantage is that commercial CCD and CMOS cameras are becoming smaller and less expensive. Therefore, the use of low-cost CMOS cameras allows the construction of relatively inexpensive measurement modules suitable for measuring an entire spherical pattern. In addition, CMOS cameras may be used with a built-in pixel processor that allows individual pixels to be cleared as they become saturated. This allows neighboring pixels to remain unaffected by potential blooming problems.

Single image acquisition devices 162 (FIG. 9A) are also available that can acquire video signals from multiple detector modules simultaneously. As can be seen in FIG. 8B, there are many measurement module signals to process; therefore, it is advantageous to process them as quickly as possible. This can be done by having a single processor for each measurement module or by feeding each measurement module into a multiplexer for consecutive processing. In the preferred embodiment of the invention, six measurement modules are used for hemispherical coverage and 12 for spherical coverage. Accordingly, the parallel acquisition capability is preferred.

It is anticipated that further improvements and advantages may be derived from the invention by the use color cameras and white light sources, as well as the use of color cameras and multiple lasers, for multi-spectral scattered light imaging. In the Shack-Hartman mode, non-coherent light sources can be used to measure light-scatter intensity and phase.

Those skilled in the art will understand that the preceding exemplary embodiments of the invention provide the foundation for numerous alternatives and modifications that are also deemed within the scope of the invention. For example, the detector modules 12 and the lenses 14 could be replaced with a single hemispherical or spherical surface composed of light detectors. The hemispherical or spherical surface could be made up of flexible material with flexible camera circuitry embedded or printed on the material. A combination of phase-only and intensity-only measurement modules could be used in the same hemispherical or spherical structure, allowing for the measurement of only intensity in certain regions of the scatter field while both intensity and phase are measured in other parts of the same scatter field.

Thus, while the invention has been shown and described herein in what are believed to be the most practical and preferred embodiments, it is recognized that departures can be made therefrom by those skilled in the art. Therefore, the invention is not to be limited to the disclosed details but is to be accorded the full scope of the claims to embrace any and all equivalent apparatus and methods.

I claim:

1. A device for measuring light propagated from a point source on a sample surface, comprising:
   a stage for holding the sample surface;
   a plurality of multi-pixel sensors adapted to measure intensity values of light fractions propagated radially from said point source on the sample surface; and
   an optical system including a plurality of lenses arranged in a hemispherical configuration for collimating a predetermined portion of said light fractions toward one of the plurality of multi-pixel sensors so that each of said portions of light fractions is received by a corresponding set of pixels in said one of the plurality of multi-pixel sensors.

2. The device of claim 1, wherein said plurality of lenses includes at least one aspheric lens.

3. The device of claim 1, wherein said plurality of multi-pixel sensors is distributed over a support structure of spherical geometry and said sample surface is positioned on an equatorial plane of the support structure.

4. The device of claim 1, further including a test light source adapted to illuminate the sample surface with a test beam at a predetermined angle of incidence to produce said light propagated from the point source on the sample surface.

5. The device of claim 4, further including a reference light source adapted to illuminate a reference surface with a reference beam, and wherein at least one of said plurality of multi-pixel sensors is an interferometer adapted to measure a plurality of interferograms resulting from interference between the light propagated from the point source and the reference beam produced by the reference light source.

6. The device of claim 5, wherein the reference surface is substantially coextensive with a portion of the sample surface.

7. The device of claim 6, wherein said test beam is converging and said interferometer is a phase-shifting interferometer adapted to produce said reference beam from the test beam by reflecting a portion of the test beam from a convex lens and by directing the reference and test beams collinearly toward the sample surface.

8. The device of claim 6, wherein said interferometer comprises means for producing orthogonally polarized reference and test beams directed collinearly toward the sample surface and a polarization phase-shifting interferometer.

9. The device of claim 1, wherein said plurality of multi-pixel sensors comprises a plurality of phase sensors adapted to measure phase values of said light fractions propagated radially from the point source on the sample surface.

10. The device of claim 9, wherein said phase sensors are Shack-Hartman sensors.

11. The device of claim 4, wherein said plurality of multi-pixel sensors includes a plurality of phase sensors adapted to measure phase values of said light fractions propagated radially from the point source on the sample surface.

12. The device of claim 11, wherein said phase sensors are Shack-Hartman sensors.

13. A device for measuring light scattered radially from a point source on a sample surface, comprising:
   a substantially hemispherical structure defining an equatorial plane;
   a stage for holding the sample surface at a position substantially on said equatorial plane;
   a test light source adapted to illuminate the sample surface at a predetermined angle of incidence;
   a plurality of multi-pixel sensors adapted to measure intensity values of light fractions scattered radially toward discrete portions of an interior surface of the substantially hemispherical structure; and
   an optical system for collimating said light fractions toward said plurality of multi-pixel sensors, said optical system including a plurality of lenses arranged in a hemispherical configuration over said substantially hemispherical structure.

14. The device of claim 13, wherein said test light source illuminates the sample surface through an orifice in the substantially hemispherical structure.

15. The device of claim 13, wherein said plurality of multi-pixel sensors is adapted to measure intensity values of light fractions scattered toward substantially all of said interior surface of the substantially hemispherical structure.

16. The device of claim 13, further including a second optical system for collimating a portion of said light fractions toward one of the plurality of multi-pixel sensors so that said portion of said light fractions is received by a corresponding set of pixels in said one of the plurality of multi-pixel sensors.

17. The device of claim 16, wherein said second optical system includes at least one aspheric lens.

18. The device of claim 13, further including a reference light source adapted to illuminate a reference surface with a reference beam and wherein at least one of said plurality of multi-pixel sensors is an interferometer adapted to measure a plurality of interferograms resulting from interference between the light scattered from the point source and the reference beam produced by the reference light source.

19. The device of claim 18, wherein the reference surface is substantially coextensive with a portion of the sample surface.

20. The device of claim 13, wherein said plurality of multi-pixel sensors comprises a plurality of phase sensors adapted to measure phase values of said light fractions scattered radially from the point source on the sample surface.

21. The device of claim 20, wherein said phase sensors are Shack-Hartman sensors.

22. The device of claim 16, wherein said plurality of multi-pixel sensors comprises a plurality of phase sensors adapted to measure phase values of said light fractions scattered radially from the point source on the sample surface.

23. The device of claim 22, wherein said phase sensors are Shack-Hartman sensors.

24. The device of claim 13, further including a second substantially hemispherical structure positioned on an opposite side of said equatorial plane; and a second plurality of multi-pixel sensors adapted to measure intensity values of transmitted light fractions scattered toward discrete portions of an interior surface of said second substantially hemispherical structure.

25. The device of claim 24, wherein said second plurality of multi-pixel sensors is adapted to measure intensity values of said transmitted light fractions scattered toward substantially all of said interior surface of the second substantially hemispherical structure.

26. The device of claim 25, further including a second optical system for collimating a portion of said transmitted light fractions toward one of the second plurality of multi-pixel sensors so that said portion of transmitted light fractions is received by a corresponding set of pixels in said one of the second plurality of multi-pixel sensors.

27. The device of claim 13, wherein said second optical system includes a plurality of aspheric lenses.

28. The device of claim 27, wherein each of said plurality of aspheric lenses is pentagonal in shape.

29. The device of claim 27, wherein said plurality of multi-pixel sensors is arranged in a polyhedral configuration defining a number of plane faces adjacent to said substantially hemispherical structure and said optical system includes a corresponding number of aspheric lenses.

30. The device of claim 1, wherein at least some of said lenses are pentagonal in shape.

31. The device of claim 30, wherein a plurality of said pentagonal shaped lenses are arranged in a substantially geodesic configuration.

32. The device of claim 28, wherein a plurality of said pentagonal shaped aspheric lenses are arranged in a geodesic configuration over said substantially hemispherical structure.

33. The device of claim 32, wherein said plurality of multi-pixel sensors is six in number and said optical system includes six corresponding pentagonal shaped aspheric lenses arranged in a geodesic configuration over said substantially hemispheric structure.

34. The device of claim 7, wherein said test beam and said reference beam are directed outside said hemispheric structure to an interferometric sensor.

* * * * *